United States Patent [19]

Adrian

[11] Patent Number: 5,569,179
[45] Date of Patent: Oct. 29, 1996

[54] ACOUSTIC CATHETER WITH MAGNETIC DRIVE

[75] Inventor: Sorin Adrian, Penn Valley, Pa.

[73] Assignee: Medelex, Inc., Penn Valley, Pa.

[21] Appl. No.: 547,743

[22] Filed: Oct. 26, 1995

[51] Int. Cl.$^6$ ................................................ A61B 17/00
[52] U.S. Cl. ................................................ 604/22; 606/1
[58] Field of Search ........................ 604/22, 264, 280;
601/2; 607/97; 606/1, 169, 171

[56] References Cited

U.S. PATENT DOCUMENTS 5,423,797  1/1995  Adrian .

Primary Examiner—Manuel Mendez
Attorney, Agent, or Firm—William H. Meise

[57] ABSTRACT

A catheter 10 according to the invention includes an elongated shaft 14 defining a distal end 12 and a proximal end 13. The proximal end of the shaft includes a coupling arrangement 15 for coupling to a rotary drive such as an external rotary motor. The catheter also includes a rotary-to-axial motion converter 28 coupled to the distal end of the shaft 14. The rotary-to-axial-motion converter 28 includes at least a first magnetic pole pair 22N, 22S mechanically coupled to the distal end of the shaft 14 for being rotated thereby along an arc. The motion converter also includes a nonrotating reciprocating follower 30, and at least a second magnetic pole pair 30N, 30S which is located so as to come within the magnetic influence of the first magnetic pole pair 22N, 22S during each the rotation of the shaft 14. During each rotation, the two magnetic poles attract or repel, for causing reciprocating axial motion of the reciprocating follower 30. In use, the reciprocal axial motion generates acoustic energy in a vas to comminute or ablate matter.

15 Claims, 4 Drawing Sheets 5,569,179

ACOUSTIC CATHETER WITH MAGNETIC DRIVE

FIELD OF THE INVENTION

This invention relates to medical catheters, and more particularly to catheters for ablation, angioplasty, and/or other medical procedures using acoustic energy or ultrasound, in which the acoustic energy is derived from a rotary shaft by magnetic coupling.

BACKGROUND OF THE INVENTION

Several hundred thousand people die in the United States each year from acute myocardial infarction, and many more suffer from chronic heart problems. A major contributing factor in both acute and chronic heart problems is a reduction in nutrient blood flow to the muscles of the heart resulting from a reduction of blood flow through the coronary blood vessels. The reduction in flow may be caused by deposits of atherosclerotic plaque on the walls of the blood vessel, which causes a narrowing of the lumen or channel of the blood vessel. When the lumen is sufficiently narrowed, the rate of flow of blood may be so diminished that spontaneous formation of a thrombus or clot occurs by a variety of physiologic mechanisms. As is known, once a blood clot has started to develop, it extends within minutes into the surrounding blood, in part because the proteolytic action of thrombin acts on prothrombin normally present, tending to split this into additional thrombin which causes additional clotting. Thus, the presence of atherosclerotic plaque not only reduces the blood flow to the heart muscle which it nourishes, but is a major predisposing factor in coronary thrombosis.

Among the treatments available for the conditions resulting from plaque formations are pharmacological means such as the use of drugs, for example nitroglycerin, for dilating the coronary blood vessels to improve flow. In those cases too far advanced to be manageable by drugs, surgical treatment may be indicated. One of the surgical techniques commonly used is the coronary bypass, in which a substitute blood vessel shunts or bypasses blood around the blockage. The bypass operation is effective, but is expensive and subject to substantial risks.

Another treatment for plaque formations is mechanical removal by means of a rotary cutter catheter, as described, for example, in U.S. Pat. Nos. 4,445,509 and 4,990,134, issued May 1, 1984 and Feb. 5, 1991, respectively, both in the name of Auth. Catheters are known in which a cutter can be driven at speeds as great as 200,000 rpm. When the cutter is applied to the arterial walls, the walls may undesirably be perforated.

Percutaneous transluminal balloon coronary angioplasty is a widely used alternative to open-heart coronary bypass surgery for the treatment of acute and chronic heart problems. This method involves insertion of a deflated balloon into the lumen of an artery partially obstructed by plaque, and inflation of the balloon in order to enlarge the lumen. The lumen remains expanded after removal of the catheter, but the obstructing material remains. Among the problems with this technique, as described in the article "Ultrasonic Plaque Ablation," by Siegel et al., published at pp 1443–1447 of Vol. 78, No. 6, December 1988 issue of the periodical Circulation, are those involved in introducing the catheter with its balloon into a blood vessel which is completely or almost completely occluded, and restenosis of the narrowed vessel after the angioplasty procedure by recurrence of the arterial plaque.

Microwave aided balloon angioplasty is described in U.S. Pat. No. 4,643,186 issued Feb. 17, 1987 in the name of Rosen et al. In the arrangement as described by Rosen et al., a catheter including a microwave transmission line terminates at its distal end in an antenna surrounded by a balloon. During angioplasty, microwave power is applied to the proximal end of the catheter and flows to the antenna, which radiates the energy to the plaque for heating and thereby softening the plaque. The balloon is expanded against the softened plaque to thereby expand the lumen of the blood vessel. While microwave heating improves balloon angioplasty, the plaque is not removed by the angioplasty, and may expand after the procedure, or if it does not expand, may provide a base upon which additional plaque may be deposited.

Another technique which has recently received a good deal of attention is transluminal laser catheter angioplasty. This treatment involves introduction into the coronary artery of a fiber optic cable, the proximal end of which is connected to a laser energy source. The distal end of the fiber optic cable is directed towards the plaque. The laser is pulsed, and the resulting high energy light pulse vaporizes a portion of the plaque. Many problems remain unsolved in laser catheter angioplasty, as in mechanical cutting catheters. When the energy of the laser discharge is directed towards the arterial walls, the walls may undesirably be perforated. Further problems relate to the difficulty in matching the characteristic of lasers and fiber optic cables to the frequency absorption characteristics of various types of plaque, and the by-products of the destruction of the plaque.

Experimental studies have shown that ultrasound or acoustic angioplasty has the potential for differentiating between normal arterial walls and abnormal walls including atherosclerotic plaques and thrombi, as described, for example, in "Experimental Ultrasonic Angioplasty:Disruption of Atherosclerotic Plaques and Thrombi in Vitro and Arterial Recanalization in Vivo," by Rosenschein et al., published at pp 711–717 of Vol. 15, No. 3, Mar. 1, 1990 issue of the J. Am. Coll. Cardiology, and in "Ability of High-Intensity Ultrasound to Ablate Human Atherosclerotic Plaques and Minimize Debris Size," by Ernst et al., published at pp 242–246 of Vol. 68 of The American Journal of Cardiology, Jul. 15, 1991. It appears that significant ultrasonic energy must be applied to the plaque in order to effect its removal. U.S. Pat. No. 3,565,062, issued Feb. 23, 1971 in the name of Kuris, describes an ultrasonic catheter including an electrodynamic, piezoelectric or magnetostrictive ultrasonic motor operating in the range of 1000 Hz to 100 KHz, which may also be operated in a swept-frequency mode. The vibrations from the motor are coupled, through an elongated transmission member which extends through the catheter, to a vibrating tool or head, shaped for removal of plaque. As described therein, when the device is operated at a fixed frequency, nodes along the transmission member are heated. U.S. Pat. No. 5,163,421, issued Nov. 17, 1992 in the name of Bernstein et al. describes the problem of heating of the transmission member, and reduction of the power transmitted to the tool due to transmission losses in the transmission member. The solution suggested in the Bernstein et al. patent is the use of a high Q material. However, even with the use of high-Q transmission members, losses in the vicinity of 50% (−3 dB) occur in ultrasonic catheters of the lengths necessary for coronary angioplasty, and these losses increase significantly at bends in the transmission member.

U.S. Pat. No. 5,423,797, issued Jan. 13, 1995 in the name of Adrian et al. describes an improved acoustic angioplasty catheter in which longitudinal acoustic waves are generated from rotary motion of a shaft by the use of a swash plate including a sinusoidal surface, for imparting a back-and-forth motion to a follower in response to the shaft rotation.

Improved angioplasty catheters are desired.

SUMMARY OF THE INVENTION

A catheter according to the invention includes an elongated shaft defining a distal end and a proximal end. The proximal end of the shaft includes a coupling arrangement for coupling to a rotary drive such as an external rotary motor. The catheter also includes a rotary-to-axial motion converter coupled to the distal end of the shaft. The motion converter includes at least a first magnetic pole mechanically coupled to the distal end of the shaft for being rotated thereby along an arc. The motion converter also includes a nonrotating reciprocating device or follower, and at least a second magnetic pole which is located so as to come within the magnetic influence of the first magnetic pole during each the rotation of the shaft. During each rotation, the two magnetic poles attract or repel, for causing reciprocating motion of the reciprocating device relative to the distal end of the shaft. This motion generates acoustic energy in the fluid medium located at the distal end of the catheter. The acoustic energy may be used for therapeutic purposes. An advantage of some of the embodiments of the invention over some of the swash-plate embodiments of the prior art is that a spring arrangement is not needed to return the follower after an excursion in one direction, which reduces heating losses in the spring and eliminates friction losses between surfaces of rotor and follower.

DESCRIPTION OF THE DRAWING

FIG. 2b is a plot of axial motion of the reciprocating head or device as a result of shaft rotation for the arrangement of FIG. 2a;

FIG. 3b is an axial view of the magnetic drive plate of FIG. 3a, FIG. 3c is a plot of axial excursion of the reciprocating device as a function of shaft rotation for the arrangement of FIG. 3a.

DESCRIPTION OF THE INVENTION

Figure 1:
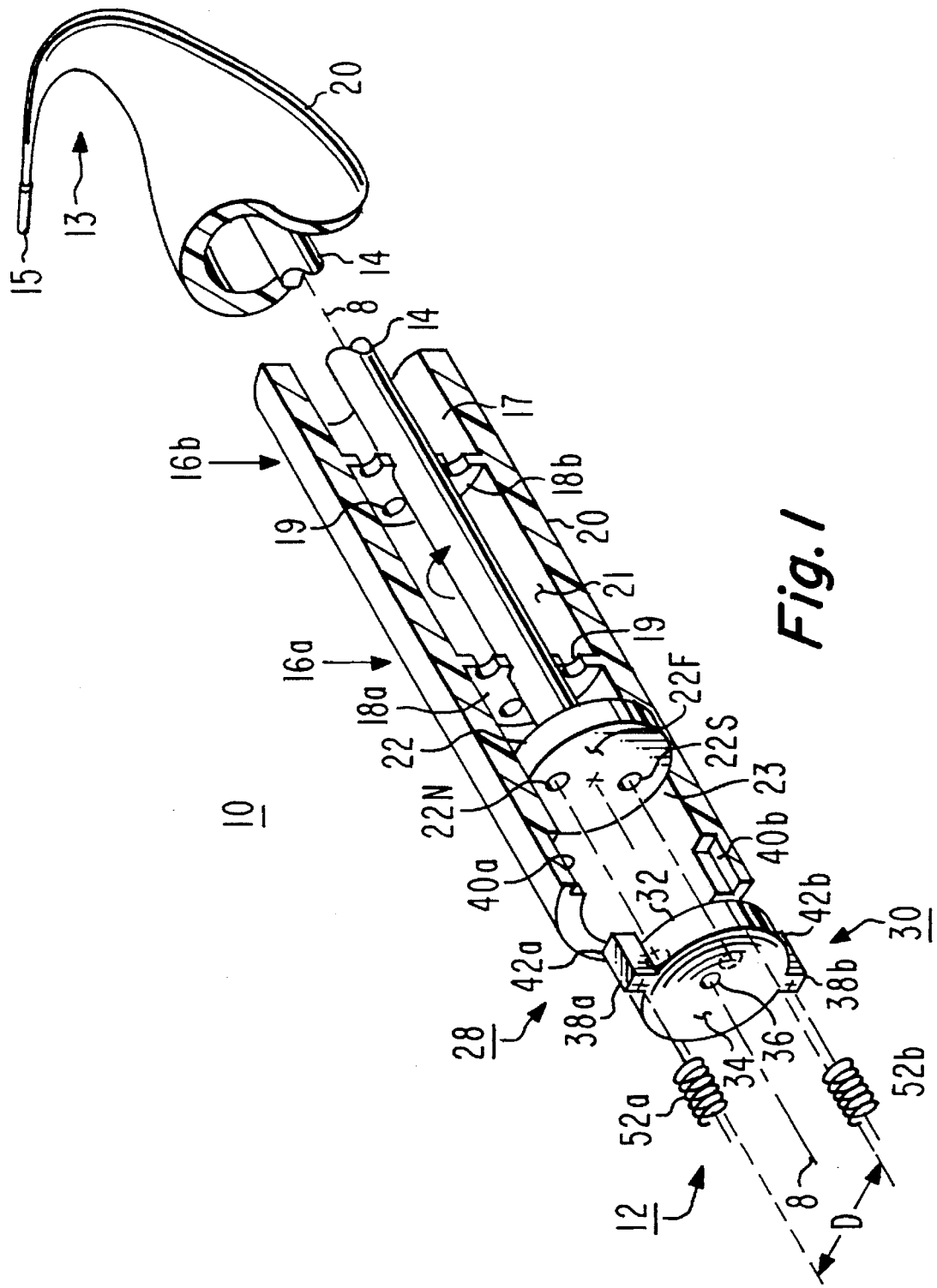
FIG. 1 is a simplified perspective or isometric view, partially cut away to illustrate interior details, of the distal and proximal ends of a catheter according to an aspect of the invention, illustrating a rotary shaft and a rotary-to-axial-motion converter including a magnetic drive and an reciprocating acoustic head.
Figure 2A:
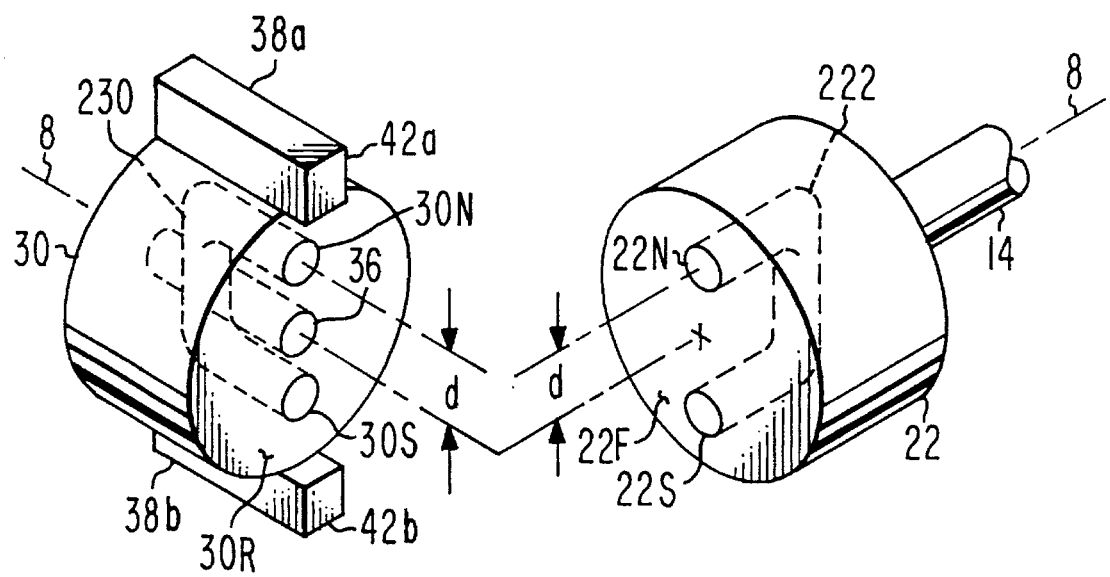
FIG. 2a is an exploded, partially cut away view of the magnetic drive and follower arrangement of FIG. 1, illustrating some details of the magnetic structure, for producing one axial excursion for each rotation of the driver.

In FIGS. 1 and 2a, the distal end 12 of a catheter 10 illustrates a flexible rotary shaft 14 capable of continuous rotation, which is adapted to be driven from a proximal end 13 at a rotary connector 15. Shaft 14 is supported about a common axis 8 at support locations 16a, 16b, along its length by bearing surfaces (not separately designated) in fenestrated bulkheads designated 18a and 18b, respectively. Some of the fenestrations are designated 19. Bulkheads 18a and 18b may be formed integrally with a flexible catheter body 20, thereby defining a longitudinal lumen 17, which may be used for aspiration, as described in the aforementioned Adrian et al. patent, or which may be used for infusing medication or dye. A magnetic drive member or plate 22 in the general form of a circular disk or plate has its "rear" or proximal surface coupled coaxially to the distal end of shaft 14 for being driven thereby in a rotary motion. Thrust bearings, not illustrated, may be used to prevent drive disk 22 from moving axially, if it is not otherwise constrained. The "front" or distal surface 22F of magnetic drive 22 is flat, unlike that of the Adrian et al. patent. Instead of using a mechanical rotary-to-axial motion driver as in Adrian et al., magnetic drive plate 22 has a pair of magnetic poles, namely a North pole 22N, and a South pole 22S. The outer periphery of magnetic drive 22 is spaced apart by a gap 23 from the inner surface 21 of catheter wall 20, to thereby define a channel or through which fluid may flow during aspiration. Aspiration suction applied to the proximal end (not illustrated in FIG. 1) of lumen 17 results in the flow of fluids through lumen 17.

Those skilled in the art will recognize that, since catheter 10 and shaft 14 of FIGS. 1 and 2a are flexible, that common axis 8 will, at any particular location, be coaxial with only adjacent portions of the catheter, and that remote portions of the catheter may have axis 8 lying relatively at skew angles.

Also visible in FIGS. 1 and 2a is a follower designated generally as 30, which coacts with the magnetic fields of poles 22N and 22S of magnetic drive 22 to form a rotary-to-axial motion converter 28. Follower 30 includes a generally circular plate-like structure coaxial with common axis 8. Follower 30 has an outer periphery 32 which defines a diameter D which fits closely within the body 20 of catheter 10, but not so closely as to restrain axial motion. Follower 30 may, if desired, define a conical or funnel-shaped front or distal surface 34 to "focus" the acoustic energy generated by the catheter, and also defines a bore 36 extending from front surface 34 through to the rear surface of follower 30, to allow the aspiration of fluids from the region being treated with acoustic energy. Follower 30 further defines two ribs, ridges or protrusions 38a and 38b, which are diametrically opposite to each other relative to common axis 8. Ribs 38a and 38b extend to a greater diameter than diameter D, and, when follower 30 is assembled into the distal end of catheter body 20, protrude into correspondingly shaped channels or grooves 40a and 40b, respectively, for preventing rotary motion of follower 30, and for allowing a small amount of axial motion. Assembly of the follower into the body 20 of the catheter 10 may be facilitated by a pair of legs 42a and 42b extending proximally by a small amount from the follower plate 30, but the legs should not be so long as to contact front surface 22F of magnetic drive 22, to avoid excess friction. A pair of springs, illustrated as 52a and 52b, may be used, if desired, to bear against follower 30 at ribs 38a and 38b, respectively, to urge the follower 30 as close to the magnetic drive plate 22 as the legs 38a, 38b sliding in channels 40a and 40b permit; however, this is not necessary, so long as the excursion of the follower is limited by appropriate stops, and has the advantage of reducing heating in the springs. The proximal surface 30R (visible in FIG. 2a) of follower 30 is flat, and parallel to its front face 34. A pair of magnetic poles 30N, 30S are held flush with the rear face 30R of follower 30. When shaft 14 is rotated by a motor or other drive, poles 22N and 22S rotate about axis 8 along an arc. At each revolution of the shaft and magnetic drive 22, magnetic pole 22N rotates once about the axis along an arc, and sequentially comes adjacent magnetic poles 30N and 30S of follower 30. For some embodiments, the proximal surface 30R of follower 30 should be as close as possible to the front or distal surface 22F of magnetic drive 22 in order to maximize the magnetic force between the relatively or mutually rotating pole pairs. At one position during the rotation cycle of magnetic drive 22, pole 22N is adjacent follower pole 30N and drive pole 22S is adjacent follower pole 30S, whereupon the adjacent or physically opposed two N poles and two S poles mutually repel, and a force is generated which tends to move the follower in a distal direction (away from the magnetic drive 22). One-half revolution later, magnetic drive pole 22N is adjacent follower pole 30S, and drive pole 22S is adjacent to follower pole 30N, with the result that the follower 30 is attracted toward the drive plate 22, and tends to move in a proximal direction (toward magnetic drive 22). Thus, during each rotation, forces are imposed between magnetic drive 22 and follower 30 which tend to move the follower axially in a back-and-forth motion. Springs 52a and 52b of FIGS. 1 and 2a, if used, are held in place, and bear against, a portion of body 20 of catheter 10 which is not illustrated, for tending to slightly urge the follower toward the drive. However, the spring force should not be greater than the magnetic force when the poles are physically opposed, or axial motion will be attenuated.

Figure 2B:
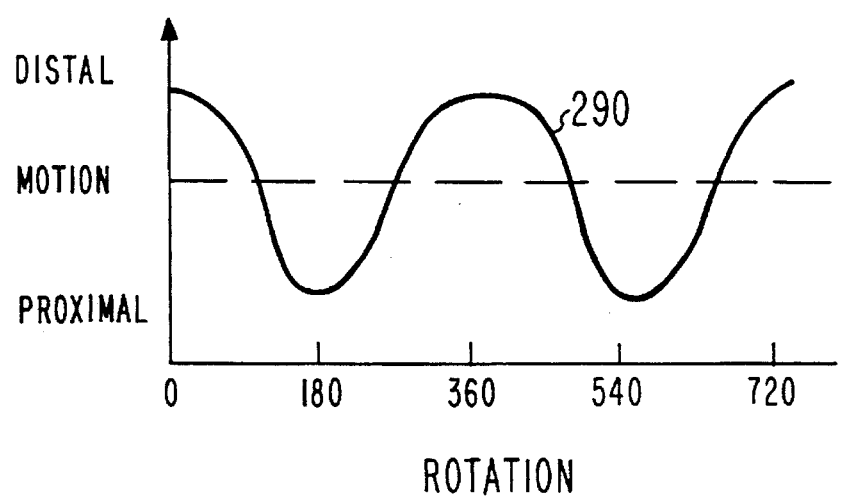

FIG. 2a is an exploded, partially cut away view of the magnetic drive and follower arrangement of FIG. 1, illustrating some details of the magnetic structure. In FIG. 2, the mating or mutually adjacent faces of the magnetic drive 22 with the follower 30 are visible. More particularly, pole 22N and 22s flush with face 22F of magnetic drive 22 are visible, each at a distance d from axis 8 of rotation. The magnetic drive disk 22 and the follower disk 30 are made from a nonmagnetic substance, such as a polymer or a nonmagnetic metal. The magnetic poles 22N and 22S are illustrated as being connected together by a magnetic "horseshoe" structure 222 extending within magnetic drive plate 22, which provides a return path for the magnetic fields behind face 22F, so as to maximize the fields in the gap between the magnetic drive 22 and the follower 30. Similarly, North magnetic poles 30N and 30S are visible, flush with the proximal or rear surface 30R of follower 30, connected together by a corresponding magnetic structure 230, which provides a return path for the magnetic fields behind face 30R, so as to maximize the fields in the gap, and to maximize the interaction with the magnetic fields of the magnetic drive. Such magnetic return paths are well known to those skilled in the electrical arts, and especially arts related to electrical motors. In the illustrated rotational position of the magnetic drive 22 relative to follower 30, the North poles 22N and 30N are juxtaposed, and the South poles 22S and 30S are juxtaposed. In the illustrated positions, the mutually adjacent N poles repel, and the mutually adjacent S poles also repel each other. Consequently, there is a repulsive force between drive 22 and follower 30, which tends to move them apart. The repulsive force diminishes during the next following quarter-rotation of magnetic drive 22, and then an attractive force builds up for the succeeding quarter-rotation. The attractive force peaks when the driver N pole 22N is adjacent the follower S pole 30S, at which time driver S pole 22S is also adjacent follower N pole 30N. The attractive force tends to pull the driver and the follower together. During the next half-rotation of the driver, the attractive force diminishes, and a repulsive force once again builds up. Thus, each rotation of the magnetic drive 22 results in one back-and-forth axial excursion of the follower. FIG. 2b illustrates a plot 290 of axial motion resulting from rotation of magnetic drive 22 of FIGS. 1 and 2a, illustrating one back-and-forth excursion per rotation.

In operation of the arrangement of FIG. 1, catheter 10 is introduced into a vas or blood vessel of a patient to be treated, whereby the distal face 34 of follower 30 is adjacent the treatment site, and is surrounded by liquid such as blood, or by a transparent liquid if the catheter includes a fiber optic scope. Shaft 14 is rotated at a high speed, for example 200,000 rotations per minute (RPM), and magnetic drive 22 rotates accordingly. With each rotation of the magnetic drive, a given pole pair will result in one fore-and-aft motion of the follower. A rotational speed of 200,000 RPM corresponds to 3333 rotations per second, which in turn results in 3333 front-to-rear excursions of the follower, corresponding to 3333 Hz, well within the acoustic range. The magnitude of the repulsive or attractive force is determined by the strength of each magnetic pole pair, their axial separation, and the number of magnetic pole pairs which come into alignment at one time. The amount of motion of the follower depends upon the magnitude of the force at each confluence of the magnetic poles, and upon the inertia of the follower, and is limited by the length of grooves 40a, 40b. The desired amount of motion may range from about 10 microns to 500 microns, although special conditions may require excursions outside this range. The front-to-rear excursions of follower 30 couple energy into the surrounding medium, which will most commonly be liquid, and generates acoustic energy. The acoustic energy is coupled through the medium to such tissue or unwanted deposits as may be contacted. The follower is applied to the region to be treated in a manner similar to that known, for ablating or cutting atherosclerotic plaque or other material with the aid of the acoustic energy generated by the follower.

Also during operation of the arrangement of FIG. 1, the acoustic energy generated by follower 30 will dislodge or comminute matter in the vas, which may be removed by applying aspirating suction to the proximal end of catheter 10. The aspirating suction will be communicated through fenestrations 19 in bulkheads 18a, 18b, . . . , through gap 23 between the outer edge of magnetic drive 22 and the inner surface 21 of catheter body 20, through the gap between the distal face 22F of magnetic drive 22 and the proximal face 30R of follower 30, and finally through bore 36 in follower 30. The aspirating suction will result in a flow of fluid including the dislodged matter, which prevents it from circulating through the body of the patient.

A principal advantage of the arrangement according to the invention, as described in conjunction with FIG. 1, is that little power is lost or dissipated in the drive coupler (the magnetic drive arrangement) by comparison with the prior art swash plate arrangement, with a concomitant decrease in unwanted heating of the structure, wear of the swash plate, and somewhat reduced vibration or noise.

Figure 4:
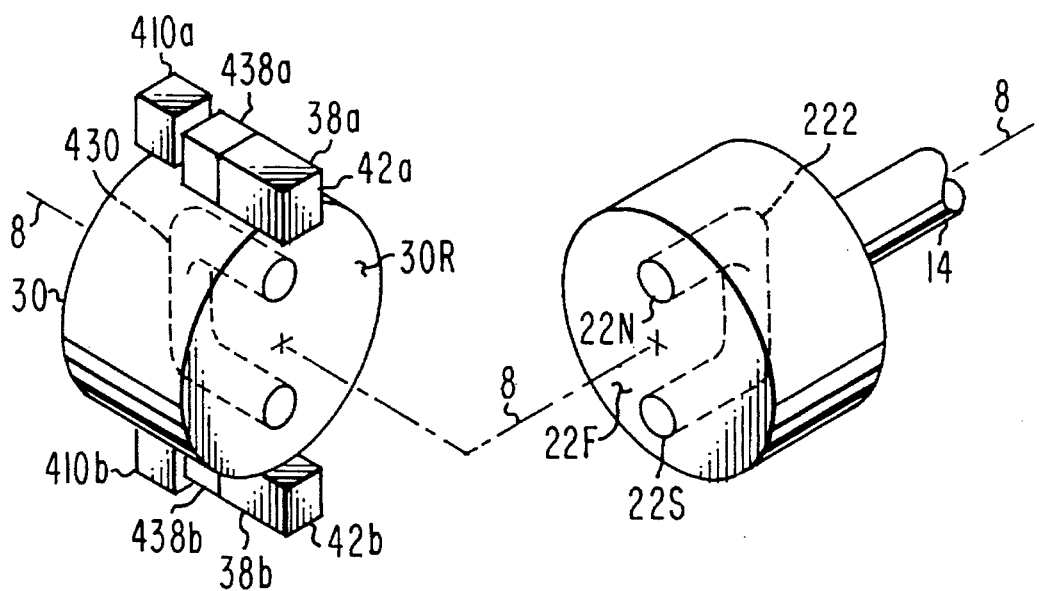
FIG. 4 is a simplified view similar to that of FIG. 2a, in which magnetized materials are used in the magnetic driver, and nonmagnetized, magnetically permeable material is used in the follower.

While the arrangement of FIG. 1 and FIG. 2 as so far described includes permanently magnetized material in both the driver and in the follower, only one set of permanent magnets is necessary. The embodiment of FIG. 4 is similar to the arrangement of FIG. 2a, in that the magnetic poles (22N and 22S illustrated) of driver 22 are permanently magnetized, but the magnetic or magnetically permeable structure 430 associated with follower 30 is not magnetized. During rotation of magnetic driver 22, the attractive force will still occur at each rotation of the driver, but, instead of a repulsion at the 180° rotation point, a second attraction will occur. Thus, a frequency doubling will occur with a loss of half the amplitude of the axial motion. The arrangement of FIG. 4 does not use a spring for returning the follower to a distal position between attractions by the magnetic structure of the driver 22, but instead uses a second arrangement of magnets. More particularly, in FIG. 4, the ribs, ridges or protrusions 38a and 38b, which prevent rotation of the follower by their interaction with the body of the catheter, have magnetic portions designated 438a and 438b. A pair of magnets illustrated as 410a and 410b are affixed to the body of the catheter (not illustrated in FIG. 4) adjacent to magnetic portions 438a and 438b, to interact therewith, and to provide a force tending to restore follower 30 to a distal position, whenever magnet 222 of magnetic drive 22 is not attracting magnetic structure 430 of the follower 30. While the permanent magnets have been described as being on the driver in the arrangement of FIG. 4, and the nonmagnetized magnetic material on the follower, the catheter will work equally well with the permanent magnets on the follower, and the nonmagnetized magnetically permable material on the driver; the terms "magnetic driver" and "follower" must be interpreted accordingly.

Figure 3A:
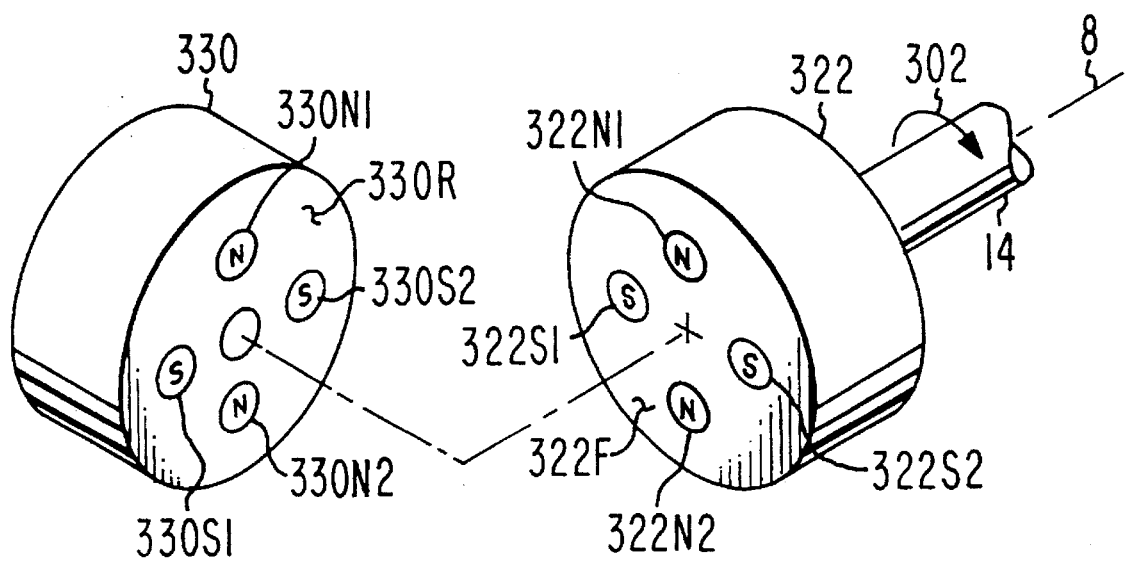
FIG. 3a is a perspective or isometric view which illustrates a magnetic drive and follower arrangement similar to that of FIG. 2a, but in which more than one back-and-forth axial excursion of the reciprocating device occurs for each rotation of the magnetic drive.
Figure 3B:
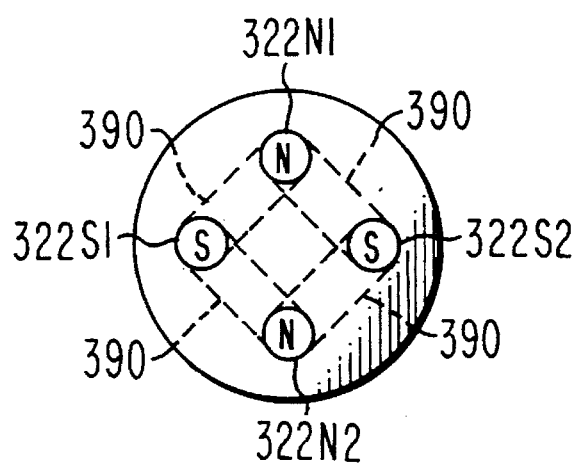
Figure 3C:
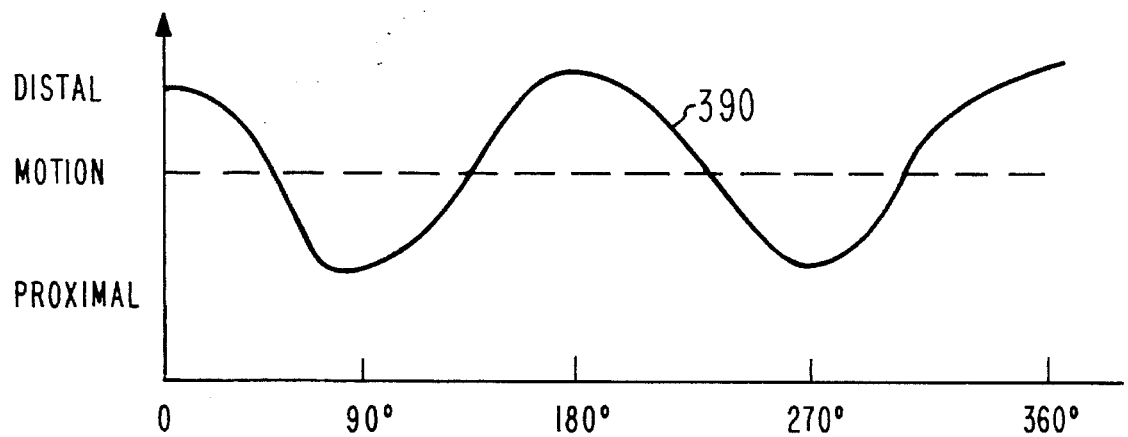

FIG. 3a illustrates a magnetic drive and follower arrangement in which more than one back-and-forth axial excursion occurs for each rotation of the magnetic drive. In FIG. 3a, a magnetic drive disk 322 is made from a magnetic material, which is magnetized on its front or distal surface 322F to form North poles 322N1 and 322N2, and corresponding South poles 322S1 and 322S2, with magnetic fields, illustrated as dash-line paths 390, extending between each N pole and its one, two or more adjacent S poles, as known in the art. Also in FIG. 3a, follower 330 is similarly made from a magnetizable material, which is surface-magnetized with a corresponding pattern of N poles 330N1 and 30N2 and S poles 330S1 and 330S2. In the illustrated positions of the magnetic drive 322 relative to follower 330, N poles 322N1 and 330N1 are adjacent, and the S poles are adjacent, so a magnetic repulsion force results, tending to cause axial motion of the follower in a distal direction. One-quarter revolution later in the direction of motion indicated by arrow 302, magnetic drive disk 322 will have its N pole 322N1 adjacent S pole 330S1 of follower 330, and all the other poles of drive 322 are physically adjacent opposite magnetic poles of the follower 330, as for example N pole 322N2 is adjacent S pole 330S2, and S poles 322S1 and 322S2 are adjacent 330N1 and 330N2, respectively, so follower 330 is attracted distally. A further quarter-rotation later in the direction of arrow 302 (a total rotation of 180°), the N poles of magnetic driver 322 are again both adjacent N poles of the follower 330, and the S poles of driver 322 are adjacent S poles of follower 330, so repulsion takes place. It can readily be seen that two axial excursions take place for each rotation of the shaft 14 with the magnetic structure of FIG. 3a, as illustrated in plot 390 of FIG. 3c. The surface-magnetized magnetic disk has the advantage of being better balanced than the arrangement of FIG. 2a, can be somewhat thinner and possibly lighter in spite of the need for a magnetic material, and can more easily accommodate longitudinal bores for the aspiration of fluids. It also does not need as high a rotational speed of the shaft to achieve an equivalent acoustic frequency; the four-pole arrangement of the magnetic drive and follower of FIG. 3a requires a shaft speed of only 100,000 rpm to achieve an acoustic frequency of 3333 Hz. This reduced shaft speed, in turn, reduces heating and wear on the shaft bearings.

Other embodiments of the invention will be apparent to those skilled in the art. For example, the spacing of the front surface 22F of rotating magnetic drive 22 from the rear surface 30R of follower 30 should be large enough, in some embodiments, to allow clearance for platelets and other components of blood. The catheter and its associated equipment can be optimized for operation at a selected acoustic frequency. For example, the shape of distal or acoustic coupling surface 34 of follower 30 can be optimized at the selected frequency to distribute the acoustic energy in a desired manner, or an accessory for shaping the acoustic energy distribution may be affixed to front face 34 of follower 30. Similarly, the greater acoustic frequency available at a given shaft speed in some embodiments may permit treatment under conditions in which treatment could not be performed in the prior art. While the illustrations provide aspiration through the gap between the magnetic drive and the magnetic follower, the magnetic drive disk may include one or more additional bores extending from the front face to the rear face, as illustrated, for example, by bore 392 in FIG. 3b. While the number of magnetic poles on the magnetic driver has been illustrated as being equal to the number on the magnetic follower, they may have different numbers of poles to achieve various frequencies in response to rotation of the magnetic driver. While a pair of springs 52a, 52b have been illustrated, a single coaxial spring can also be used to urge the follower toward the magnetic drive plate. A catheter according to the invention may include standard catheter accessories and portions which have not been explicitly described, such as a guide wire (which may be coaxial or non-coaxial), or an optical fiber scope for viewing or for application of laser energy, or microwave transmission lines or generators for application of microwave energy to the region being treated. Additional lumens may be provided for infusion of fluids, or for balloon inflation. Sensing instruments may be combined with the inventive catheter, and electrical connections therefor.

What is claimed is:

1. A catheter, comprising:

an elongated shaft defining a distal end and a proximal end, said proximal end including coupling means adapted for coupling to a rotary drive; and rotary-to-axial motion conversion means, said conversion means including at least a first magnetically influenced pole mechanically coupled to said distal end of said shaft for being rotated thereby along an arc, said conversion means further including nonrotating means capable of axial motion, said nonrotating means comprising at least a second magnetically influenced pole, and which is located so as to come within the magnetic influence of said first magnetically influenced pole during each said rotation of said shaft, for at least one of attracting and repelling said nonrotating means relative to said distal end of said shaft.

2. A catheter according to claim 1, wherein one of said first and second magnetically influenced poles is permanently magnetized.

3. A catheter according to claim 2, wherein the other one of said first and second magnetically influenced poles is permanently magnetized.

4. A catheter according to claim 1, wherein said rotary-to-axial motion conversion means comprises:

a magnetic driver affixed to said distal end of said shaft, and including at least one North magnetic pole and one South magnetic pole, at least one of said North magnetic pole and one South magnetic pole of said magnetic driver facing said nonrotating means.

5. An acoustic catheter defining proximal and distal ends, said catheter comprising:

a magnetic follower located at said distal end of said catheter, and arranged for axial motion and to prevent rotation, said magnetic follower including at least one magnetically influenced pole pair located in a first plane near a proximal surface of said magnetic follower, and at a particular distance from an axis;

a magnetic driver located arranged for rotation about said axis, said magnetic driver including a body and at least one magnetically influenced pole pair, the magnetic poles of said pole pair of said magnetic driver rotating, in consonance with said magnetic driver, in a second plane about said axis which is adjacent to said first plane, and at said particular distance from said axis, whereby rotation of said magnetic driver about said axis causes said magnetic poles of said pole pair of said magnetic driver to rotate along an arc which brings said magnetically influenced poles of said magnetic driver into the influence of the fields of said magnetic poles of said magnetically influenced pole pair of said follower, whereby said follower tends to move axially in response to said rotation of said magnetic driver; and a shaft extending through said catheter from said proximal end to said magnetic driver, for coupling rotational drive forces from said proximal end of said catheter to said magnetic driver.

6. A catheter according to claim 5, wherein said magnetic follower has the same number of magnetic poles as said magnetic driver.

7. A catheter according to claim 6, wherein said magnetic material is permanently magnetized.

8. A catheter according to claim 5, wherein said magnetic driver comprises a nonmagnetic body supporting a magnetic material.

9. A catheter according to claim 5, wherein said follower comprises a nonmagnetic body supporting a magnetic material.

10. A catheter according to claim 9, wherein said magnetic material of said nonmagnetic body of said follower is permanently magnetized.

11. A catheter according to claim 5, wherein said magnetic driver comprises a disk of magnetically influenced material.

12. A catheter according to claim 11, wherein said disk of magnetically influenced material of said magnetic driver is surface magnetized.

13. A catheter according to claim 5, wherein said follower comprises a disk of magnetically influenced material.

14. A catheter according to claim 13, wherein said disk of magnetically influenced material of said follower is surface magnetized.

15. A method for acoustic angioplasty, comprising the steps of:

introducing into a vas a catheter including a shaft and a rotational drive arrangement coupled to the distal end of said shaft;

rotating said shaft, thereby rotating said rotational drive arrangement;

holding a follower in said catheter in a manner which prevents rotational motion but allows axial motion;

magnetically coupling said rotational drive arrangement to said follower, for creating reciprocating axial forces on said follower, whereby said rotation of said shaft is magnetically coupled to said follower as reciprocationg axial motion; and providing a fluid medium at the distal end of said follower, whereupon acoustic energy is generated in said medium.

* * * * *